United States Patent [19]

Aboczky

[11] Patent Number: 5,571,111
[45] Date of Patent: Nov. 5, 1996

[54] INSTRUMENT FOR ORIENTING, INSERTING AND IMPACTING AN ACETABULAR CUP PROSTHESIS INCLUDING PROSTHESIS RETAINING HEAD ARRANGEMENT

[76] Inventor: Robert I. Aboczky, 323 E. Saddle River Rd., Upper Saddle River, N.J. 07458

[21] Appl. No.: 432,569

[22] Filed: May 1, 1995

[51] Int. Cl.$^6$ ..................................................... A61F 2/34
[52] U.S. Cl. ............................................. 606/91; 606/99
[58] Field of Search .......................... 606/90, 91, 86, 606/99; 623/22, 23

[56] References Cited

U.S. PATENT DOCUMENTS

| | | | |
|---|---|---|---|
| 4,716,894 | 1/1988 | Lazzeri et al. | 128/92 |
| 5,061,270 | 10/1991 | Aboczky | 606/91 |
| 5,169,399 | 12/1992 | Ryland et al. | 606/91 |
| 5,417,696 | 5/1995 | Kashuba et al. | 606/91 |

FOREIGN PATENT DOCUMENTS 0535973  4/1993  European Pat. Off. .

*Primary Examiner*—Michael Powell Buiz
*Assistant Examiner*—Mark S. Leonardo
*Attorney, Agent, or Firm*—Anthony F. Cuoco; Siegmar Silber

[57] ABSTRACT

An instrument for implanting an acetabular cup prosthesis includes a head adapted for supporting a selected one of a plurality of prostheses of various sizes carried on one end of the instrument. The instrument is effective for orienting, inserting and impacting the selected prosthesis for implantation, after which the instrument is removed from the implanted prosthesis.

14 Claims, 3 Drawing Sheets

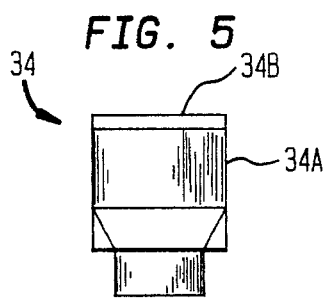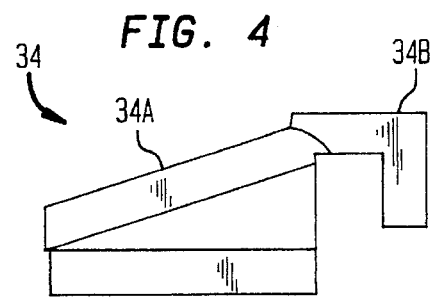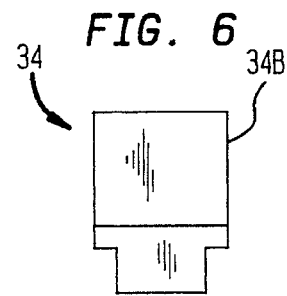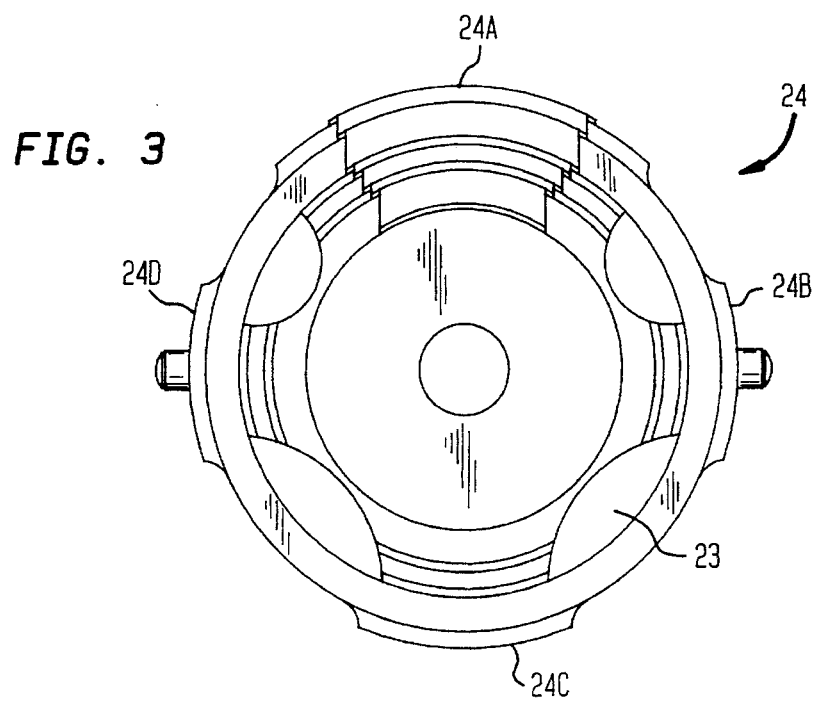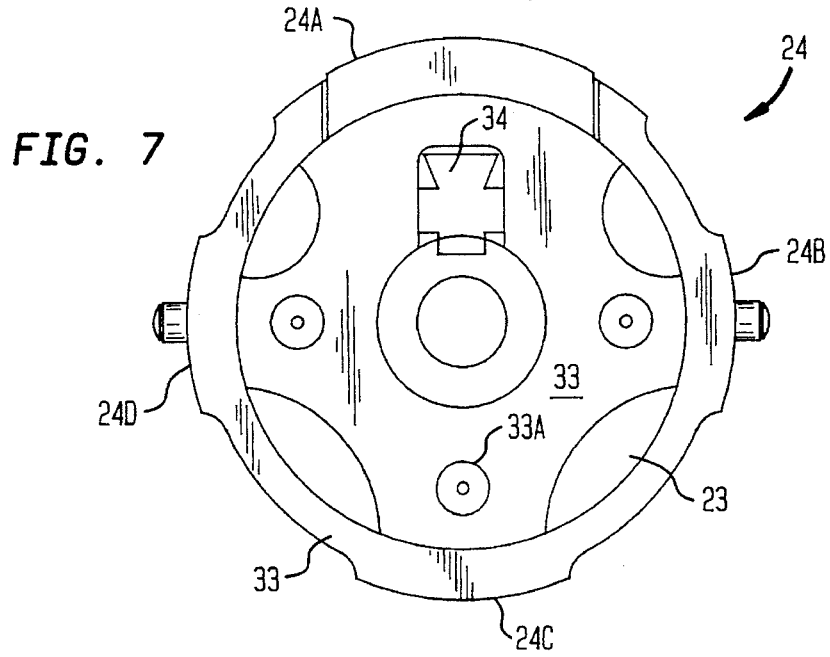

INSTRUMENT FOR ORIENTING, INSERTING AND IMPACTING AN ACETABULAR CUP PROSTHESIS INCLUDING PROSTHESIS RETAINING HEAD ARRANGEMENT

BACKGROUND OF THE INVENTION

Total hip replacement procedures have been developed which include implanting an acetabular outer shell or cup prosthesis after appropriately preparing the acetabulum for the implantation. The actual implantation includes orienting, inserting and impacting the prosthesis in the acetabulum.

A variety of separate instruments have been required to accomplish the implantation. This has been found to be disadvantageous, particularly in view of the time and inconvenience required in switching from one instrument to another, which prolongs the overall operative time. In this connection it will be noted that a major problem encountered in performing surgical procedures such as herein referred to is the risk of infection of the operative area. This risk increases as the operative time increases, and hence it is most desirable to shorten the operative time to the greatest extent possible. Moreover, due to the nature of the procedure, it is imperative that it be performed under circumstances most auspicious to the patient and to the surgeon.

The invention disclosed in U.S. Pat. No. 4,994,064 issued on Feb. 19, 1991 to the present inventor overcomes the aforenoted disadvantages and simplifies the implantation, in that only one instrument is required for all of the segments of the procedure. With the instrument therein described an estimated fifteen to twenty minutes of operative time is saved, which is desirable for the reasons aforenoted.

The invention disclosed in U.S. Pat. No. 5,037,424 issued on Aug. 6, 1991 to the present inventor is an improvement over that disclosed in U.S. Pat. 4,994,064 in that a locking arrangement is provided for the several operative members of the instrument thereby facilitating the use thereof, and a more versatile prosthesis alignment arrangement is provided to accommodate a variety of implantation situations as may from time to time occur.

The instruments disclosed in the aforementioned prior art require several operative members which co-act to grip the prosthesis so that said prosthesis can be oriented, inserted and impacted for being properly seated, after which the instruments are released from the gripped prosthesis.

The invention described in U.S. Pat. No. 5,061,270 issued on Oct. 29, 1991 to the present inventor discloses a system for the purposes described including a simplified instrument and a disposable adapter for engaging the prosthesis removably retained thereby. The adapter engages the prosthesis in snap fit relation and the instrument removably supports an alignment arrangement whereby the system is effective for orienting, inserting and impacting the prosthesis in the acetabulum.

It will be recognized that the system disclosed in U.S. Pat. No. 5,061,270 is useful for a prosthesis of a particular size commensurate with the size of the adapter. Prostheses of varying sizes require that the adapter be changed to one of a size corresponding to the size of a selected prosthesis. When considering the arrangement of U.S. Pat. No. 5,061,270 it is discerned that it would be advantageous to have a system with the capability of accepting a plurality of prostheses, without the necessity for changing adapters, prosthesis retaining members, or the like, and including means for retaining a selected prosthesis until said selected prosthesis has been properly seated.

Accordingly, it is the object of the present invention to provide an instrument for orienting, inserting and impacting an acetabular cup prosthesis in a prepared acetabulum as part of a total hip replacement procedure, wherein a wide variety of implantation procedures can be accomplished with greater facility than has heretofore been the case. The instrument includes a head arrangement for accepting a selected one of a plurality of prostheses of various sizes and for retaining the selected prosthesis on the head until the prosthesis is seated.

SUMMARY OF THE INVENTION

This invention contemplates an instrument for orienting, inserting and impacting an acetabular cup prosthesis for implanting said prosthesis in the acetabulum. The instrument includes a head adapted for supporting a selected one of a plurality of prostheses of various sizes carried on one end of the instrument. The instrument further includes a cylinder which supports the head on one end and a spring biased rod displaceably supported therein, with one end of the rod extending beyond the head end of the cylinder.

The head is generally in the form of a truncated right circular cone having a base spaced away from the extending rod end and a plurality of steps of decreasing diameters extending from the base toward the extending rod end. The head has a plurality of sectors, with one of the sectors being displaceable away from and toward the other sectors via a longitudinally displaceable key arrangement. The steps on the head are each configured to accept a prosthesis of a particular size in a substantially loose fit relationship. The one head sector is displaced away from the other sectors to create a friction force for retaining a selected prosthesis on a corresponding step.

The end of the instrument opposite the head end is arranged to receive an alignment arrangement for orienting the prosthesis to accommodate a variety of implantation procedures. The prosthesis so oriented is inserted into the acetabulum. Upon the prosthesis being so oriented and inserted, the instrument is impacted, whereby the prosthesis is seated in the acetabulum either by way of a press fit or by cementing, as the case may be.

Upon the prosthesis being seated, the rod is displaced against the spring bias to overcome the prosthesis retaining friction force exerted by the one sector section to push the head away from the seated prosthesis. The instrument is thereupon removed from the prosthesis without disturbing its seating.

BRIEF DESCRIPTION OF THE DRAWINGS

FIG. 3 is a diagrammatic front elevation view representation showing the prosthesis retaining head arrangement of the invention.

FIG. 4 is a diagrammatic side elevational view representation showing a key more generally shown in FIG. 1.

FIG. 5 is a diagrammatic front elevational view representation of the key more generally shown in FIG. 1.

FIG. 6 is a diagrammatic rear elevational view representation of the key more generally shown in FIG. 1.

FIG. 7 is a diagrammatic rear elevational view representation showing the prosthesis head arrangement shown in FIG. 3, with the key shown in FIGS. 4, 5 and 6 arranged therewith.

DETAILED DESCRIPTION OF THE INVENTION

Figure 1:
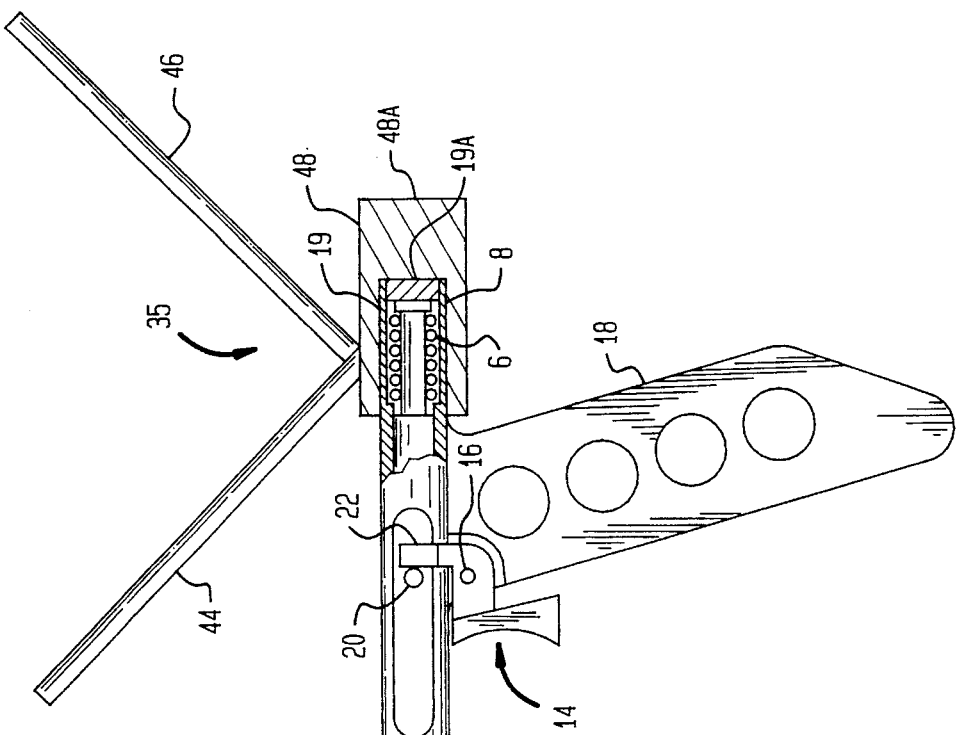
FIG. 1 is a diagrammatic, partially sectioned plan view representation showing an instrument according to the invention and arranged for orienting, inserting and impacting an acetabular cup prosthesis, and showing said prosthesis engaged thereby.
Figure 1:
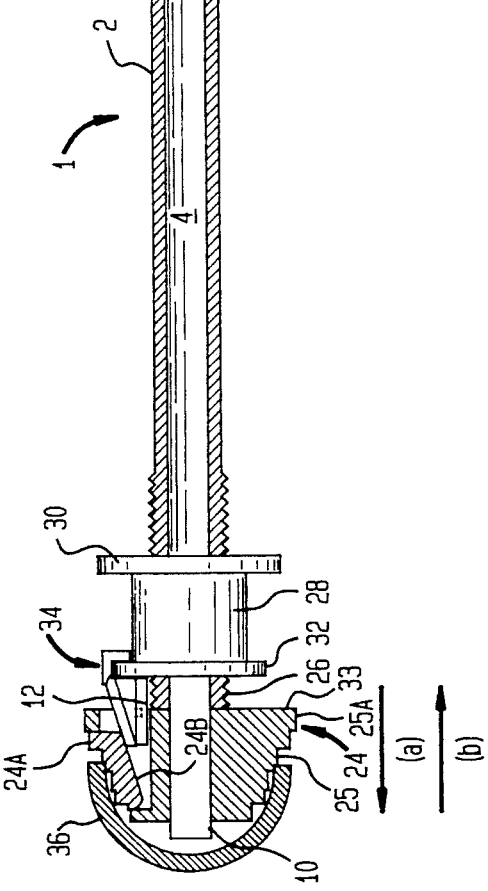

With particular reference to FIG. 1, the instrument of the invention is designated by the numeral 1. Instrument 1 includes a cylinder 2. A rod 4 is disposed in sliding relationship within cylinder 2 and is biased by a spring 6 near one end 8 of rod 4. The opposite end 10 of rod 4 extends beyond a corresponding end 12 of cylinder A trigger arrangement 14 is pivotally mounted via a pivot pin 16 to a handle grip 18 which is integral with cylinder 2 near an end 19 opposite end 12 thereof and extends generally downwardly therefrom. Rod 4 carries a transversely extending pin 20 which abuts an actuating arm 22 of trigger 14. Thus, when trigger 14 is squeezed actuating arm 22 is effective via transversely extending pin 20 for displacing rod 4 out of cylinder 2 in the direction shown by arrow (a) in the figure. When trigger 14 is released, rod 4 retracts into cylinder 2 in the direction shown by arrow (b).

Cylinder 2 has a head 24 in the form of a truncated right circular cone integral with end 12 thereof. Cylinder end 12 has an externally threaded portion 26 extending rearwardly from head 24 toward cylinder end 19. An internally threaded sleeve 28 is in threaded engagement with cylinder portion 26. Sleeve 28 includes an operating knob 30 and a displacing knob 32 in spaced relation with knob 30. Displacing knob 30 engages a key 34 for actuating head 24 to accept and retain a selected prosthesis 36 as will hereinafter be described.

End 19 of cylinder 4 is adapted to receive an alignment arrangement designated generally by the numeral 35. Alignment arrangement 35 fits over end 19 of cylinder 4 and is removably retained thereon as by a detent arrangement or the like (not otherwise shown). The purpose of alignment arrangement 35 is described in he aforenoted U.S. Pat. No. 5,061,270, said description being incorporated herein by reference.

With continued reference to FIG. 1, head 24 in the form of a truncated right angular cone as aforenoted, includes a plurality of steps such as 25 of decreasing diameters extending away from the base 25A of the cone. Head 24 has a plurality of sectors shown as four in number and designated by the numerals 24A, 24B, 24C and 24D in FIGS. 3 and 7, and which sectors are separated by fluted areas such as 23. Sector 24A is displaceable away from and toward the other sectors via key 34 as particularly shown in FIG. 1 and as will be hereinafter further described.

A particular size prosthesis 36 having a generally concave surface is disposed on a correspondingly sized step 25 of head 24, and which step has a generally convex surface, as particularly shown in FIG. 1. Key 34 is displaced forwardly by displacing sleeve 28 in threaded engagement with cylinder portion 26 via knob 30, whereby sector 24A is displaced away from head 24 to exert a friction force on the prosthesis to retain the prosthesis on the head, and is displaced rearwardly by displacing the sleeve via knob 30 to relieve said friction force, as the case may be.

The configuration of key 34 is best illustrated with reference to FIGS. 4–6. Thus, the key has an inclined surface 34A and a hook member 34B. Sector 24A has a surface 24B (FIG. 1) adjacent key surface 34A so that sector 24A slides upwardly along inclined surface 34A of key 34 when the key is displaced forwardly into head 24 and slides downwardly along the inclined surface when the key is displaced rearwardly out of head 24. Hook portion 34B of key 34 engages displacing knob 32 of sleeve 28 to couple the key to the sleeve as best shown in FIG. 1.

With particular reference to FIG. 7, a plate 33, also shown in FIG. 1, is secured to base 25A of head 24 via screws or the like 33A. Plate 33 retains key 34 in engagement with head sector 24A as will now be discerned.

USE OF THE INVENTION

Figure 2:
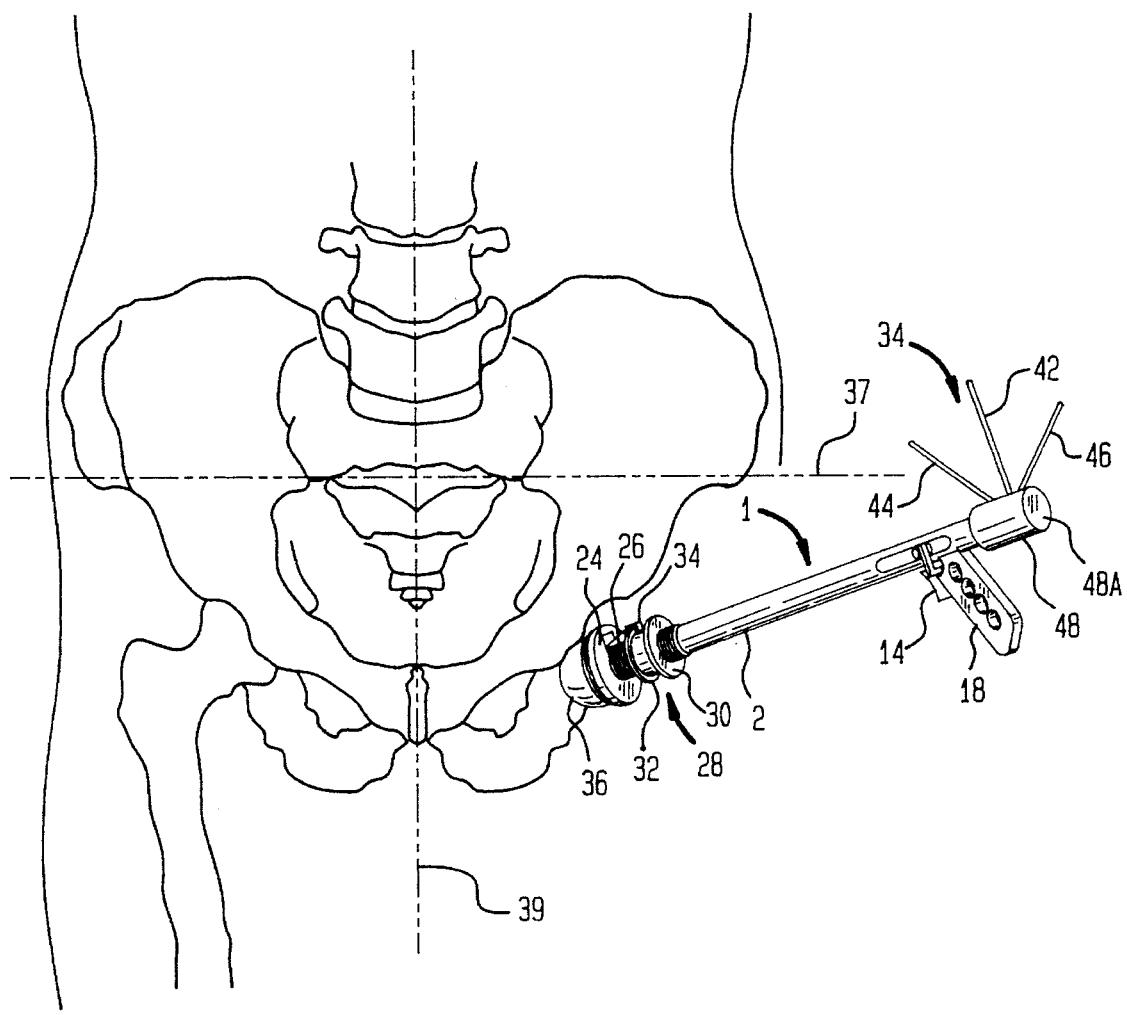
FIG. 2 is a diagrammatic representation showing a line between the right and left anterior/superior iliac spines, and which line is used for aligning the instrument of the invention.

In using instrument 1 described as aforenoted, i.e. with prosthesis 36 retained on head 24 via key 34, an alignment bar 46 of alignment arrangement 35 (FIG. 1) is disposed perpendicular to the plane in which the patient is supported, which is a substantially horizontal plane. With alignment arrangement 35 in a desired alignment position on cylinder 4, one of two alignment bars 42 or 44, depending on whether the prosthesis implantation procedure is being applied to the patient's right or left side, is aligned so as to be normal to line 37 (FIG. 2) which extends between the right and left anterior/superior iliac spines normal to the patient's pelvic line 39.

With instrument 1 thus aligned, which accomplishes the proper orientation of prosthesis 36, the prosthesis is inserted in the previously prepared acetabulum. End surface 48A of alignment arrangement cylinder 48 is impacted, whereby the prosthesis is seated in the acetabulum. Alternatively, alignment arrangement 35 may be removed from cylinder 2 and end surface 19A of end 19 of instrument cylinder 2 may be impacted to seat the prosthesis.

With prosthesis 36 so seated, trigger 14 is squeezed against the bias of spring 6 whereby rod 4 via pin 20 pushes against the prosthesis to release adapter 32 therefrom, preferably after key 34 has been displaced rearwardly to somewhat relieve the friction force exerted on prosthesis 36 as aforenoted. The instrument of the invention is thereupon removed from the seated prosthesis.

The design of the instrument is such that it retains a selected prosthesis of a plurality of prostheses in an ideal position, and holds the prosthesis firmly so that even within the bony acetabulum, the prosthesis may be maneuvered to obtain ideal alignment. The instrument itself, which may be of stainless steel or the like, has the ability to withstand high temperatures necessary for sterilization processes prior to use. Further, its simplified design renders it easy to learn its usage and to receive wide acceptability by the orthopaedic community. The particular configuration wherein a variety of prostheses can be used with the same instrument enhances the usage of the system.

The invention may be used with an acetabular prosthesis having an internal rim of any particular configuration. It will of course be understood that the engaging surface of the adapter is of the same configuration as is that of the corresponding head step. Thus, it will be understood that the system of the invention may be adapted to any implantation arrangement wherein the acetabular prosthesis has an internal surface which is circular, square, triangular, or any other shape, the same being within the scope of the invention. Likewise, the prosthesis may be of metal or may be of plastic, the same also being within the scope of the invention.

With the above description of the invention in mind, reference is made to the claims appended hereto for a definition of the scope of the invention.

What is claimed is:

1. An instrument for engaging an acetabular cup prosthesis and for orienting, inserting and impacting the prosthesis for implanting said prosthesis in the acetabulum of a patient, comprising:

an instrument cylinder having one and opposite ends corresponding to the one and the opposite ends of the instrument;

a head carried on and being integral with one end of the cylinder for removably engaging a selected one of a plurality of prostheses of different sizes, said head being in the form of a truncated right Circular cone having a base spaced away from the one cylinder end, said head, in turn, further including;

a plurality of steps of decreasing size extending away from the base toward the one cylinder end, said steps configured so that each of said steps accepts a selected prosthesis of a particular size in a substantially loose fit relationship; and a plurality of sectors, with one of the sectors being displaceable away from and toward the other sectors;

a rod disposed in sliding relation within the cylinder, and biased by a spring so that one end of the rod extends beyond the corresponding one end of the cylinder;

a sleeve in threaded engagement with the one cylinder end;

a key in engagement With the one sector and coupled to the sleeve;

displacement of the sleeve in threaded engagement with the one cylinder end in one direction being effective for displacing the key coupled to the sleeve toward the one cylinder end, whereupon the key displaces the one sector away from the other sectors to create the friction force between the key and the one sector to secure the selected prosthesis on its corresponding head step;

means for orienting the secured prosthesis carried on the opposite end of the instrument, whereupon the oriented prosthesis is inserted in the acetabulum of the patient, said means including a surface which is impacted for seating the oriented and inserted prosthesis whereupon said prosthesis is implanted on the acetabulum; and displacement of said sleeve in threaded engagement with the one cylinder end in an opposite direction being effective for displacing the key coupled to the sleeve away from the one cylinder end, whereupon the friction force between the key and the one sector is relieved for removing the instrument from the implanted prosthesis.

2. The instrument as described by claim 1, wherein the key includes:

an inclined surface adjacent the one sector, whereupon the one sector slides upwardly along the inclined surface when the key is displaced toward the one cylinder end and slides downwardly along said inclined surface when the key is displaced away from said one cylinder end.

3. The instrument as described by claim 1, including:

a plate secured to the base head and arranged with the one sector and the key for retaining said key in engagement with said one sector.

4. A system as described by claim 1, wherein the means for orienting the secured prosthesis includes:

an orienting cylinder in removable engagement with the opposite end of the instrument cylinder and adjustably positioned on said opposite end;

the orienting cylinder supporting first, second and third alignment bars, with said first and second alignment bars being in a common plane and extending away from each other with a predetermined angle therebetween;

the third alignment bar aligned perpendicular to a plane in which the patient is supported; and one of the first and second alignment bars, depending in which one of the right and left sides of the patient the prosthesis is being implanted, being aligned perpendicular to a line which extends between the patient's right and left anterior/superior iliac spines perpendicular to the patient's pelvic line, whereupon the prosthesis is oriented for implantation.

5. A system as described by claim 1, wherein:

the impacted surface is a closed end surface of the orienting cylinder when said cylinder is in removable engagement with the opposite end of the instrument cylinder.

6. A system as described by claim 1, wherein:

the impacted surface is a closed end surface of the opposite end of the instrument cylinder when the orienting cylinder in removable engagement with the instrument cylinder is removed therefrom.

7. A system as described by claim 1, including:

a hand grip arranged with the instrument cylinder near the opposite end thereof;

trigger means mounted to the hand grip and having an actuating member;

the rod disposed in sliding relation within the instrument cylinder having a pin member extending transverse to the longitudinal axis of the rod and external the instrument cylinder for engaging the actuating member of the trigger means;

the trigger means being actuated, whereupon the actuating member pushes against the pin, with the rod thereupon being operative against the bias of the spring so that the extending end thereof pushes against the implanted prosthesis to break the friction force between said prosthesis and said head; and the instrument being thereupon removed from the implanted prosthesis.

8. An instrument for engaging an acetabular cup prosthesis and for orienting, inserting and impacting the prosthesis for implanting said prosthesis in the acetabulum of a patient, comprising:

an instrument cylinder having one and opposite ends corresponding to the one and the opposite ends of the instrument;

a head carried on and being integral with one end of the cylinder for removably engaging a selected one of a plurality of prostheses of different sizes, said head being in the form of a truncated right circular cone having a base spaced away from the one cylinder end, said head, in turn, further including;

a plurality of sectors, with one of the sectors being displaceable away from and toward the other sectors;

a rod disposed in sliding relation within the cylinder, and biased by a spring so that one end of the rod extends beyond the corresponding one end of the cylinder;

means for securing the selected prosthesis on the head;

a sleeve in threaded engagement with the one cylinder end;

a key in engagement with the one sector and coupled to the sleeve;

displacement of the sleeve in threaded engagement with the one cylinder end in one direction being effective for displacing the key coupled to the sleeve toward the one cylinder end, whereupon the key displaces the one sector away from the other sectors to create the friction force between the key and the one sector to secure the selected prosthesis to said head;

means for orienting the secured prosthesis carried on the opposite end of the instrument, whereupon the oriented prosthesis is inserted in the acetabulum of the patient, said means including a surface which is impacted for seating the oriented and inserted prosthesis whereupon said prosthesis is implanted on the acetabulum; and displacement of said sleeve in threaded engagement with the one cylinder end in an opposite direction being effective for displacing the key coupled to the sleeve away from the one cylinder end, whereupon the friction force between the key and the one sector is relieved for removing the instrument from the implanted prosthesis.

9. The instrument as described by claim 8, wherein the key includes:

an inclined surface adjacent the one sector, whereupon the one sector slides upwardly along the inclined surface when the key is displaced toward the one cylinder end and slides downwardly along said inclined surface when the key is displaced away from said one cylinder end.

10. The instrument as described by claim 8, including:

a plate secured to the base head and arranged with the one sector and the key for retaining said key in engagement with said one sector.

11. A system as described by claim 8, wherein the means for orienting the secured prosthesis includes:

an orienting cylinder in removable engagement with the opposite end of the instrument cylinder and adjustably positioned on said opposite end;

the orienting cylinder supporting first, second and third alignment bars, with said first and second alignment bars being in a common plane and extending away from each other with a predetermined angle therebetween;

the third alignment bar aligned perpendicular to a plane in which the patient is supported; and one of the first and second alignment bars, depending in which one of the right and left sides of the patient the prosthesis is being implanted, being aligned perpendicular to a line which extends between the patient's right and left anterior/superior iliac spines perpendicular to the patient's pelvic line, whereupon the prosthesis is oriented for implantation.

12. A system as described by claim 8, wherein:

the impacted surface is a closed end surface of the orienting cylinder when said cylinder is in removable engagement with the opposite end of the instrument cylinder.

13. A system as described by claim 8, wherein:

the impacted surface is a closed end surface of the opposite end of the instrument cylinder when the orienting cylinder in removable engagement with the instrument cylinder is removed therefrom.

14. A system as described by claim 8, including:

a hand grip arranged with the instrument cylinder near the opposite end thereof;

trigger means mounted to the hand grip and having an actuating member;

the rod disposed in sliding relation within the instrument cylinder having a pin member extending transverse to the longitudinal axis of the rod and external the instrument cylinder for engaging the actuating member of the trigger means;

the trigger means being actuated, whereupon the actuating member pushes against the pin, with the rod thereupon being operative against the bias of the spring so that the extending end thereof pushes against the implanted prosthesis to break the friction force between said prosthesis and said head; and the instrument being thereupon removed from the implanted prosthesis.

* * * * *